US00PP11824P2

(12) United States Plant Patent
van Kesteren

(10) Patent No.: US PP11,824 P2
(45) Date of Patent: Mar. 27, 2001

(54) DELPHINIUM PLANT NAMED 'WEST END BLUE'

(75) Inventor: Mark van Kesteren, Noordwijkerhout (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/263,854

(22) Filed: Mar. 8, 1999

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Delphinium plant named 'West End Blue', characterized by its upright plant habit; dark green leaf color; bright blue flower color; and freely flowering with numerous flowers per stem.

4 Drawing Sheets

BACKGROUND OF THE INVENTION

The present invention relates to a new and distinct cultivar of Delphinium plant, botanically known as *Delphinium belladonna*, and hereinafter referred to by the cultivar name West End Blue.

The new Delphinium was discovered by the Inventor in Noordwijkerhout, The Netherlands, in 1994 in a seed bed of sown *Delphinium belladonna* seed from various crosses of unidentified Delphinium seedling selections. The new Delphinium was selected as a individual seedling in the progeny of this crossing on the basis of its unique blue flower color.

Asexual propagation of the new cultivar by vegetative cuttings and by divisions taken at Noordwikjerhout, The Netherlands, has shown that the unique features of this new Delphinium are stable and reproduced true to type in successive generations.

SUMMARY OF THE INVENTION

Plants of the cultivar West End Blue have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'West End Blue'. These characteristics in combination distinguish 'West End Blue' as a new and distinct cultivar:

1. Upright plant habit.
2. Dark green leaf color.
3. Bright blue flower color.
4. Freely flowering with numerous flowers per stem.

Compared to plants of the purple-flowered nonpatented *Delphinium belladonna* cultivar Atlantis, plants of the new Delphinium have blue flowers and darker green leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical plant of the new Delphinium in a container.

The photograph on the second sheet comprises a close-up view of typical leaves, a basal rosette leaf (left) and a flowering stem leaf (right), of the new Delphinium.

The photographs on the third and fourth sheets comprise close-up views of typical inflorescences of the new Delphinium. Flower and foliage colors in the photographs may appear different than the actual colors due to light reflectance from the leaf surface. The plant depicted in the photographs is the same age as and grown under the same environmental conditions as has been described in the detailed botanical description.

DETAILED BOTANICAL DESCRIPTION

In the following description, color references are made to The Royal Horticultural Society Colour Chart except where general terms of ordinary dictionary significance are used. Plants used for the description were one-year old plants grown under outdoor production conditions which closely approximate commercial production conditions during the spring and summer in Noordwijkerhout, The Netherlands.

Botanical classification: *Delphinium belladonna* cultivar West End Blue.

Parentage:

*Female parent.*—Unidentified *Delphinium belladonna* seedling selection.

*Male parent.*—Unidentified *Delphinium belladonna* seedling selection.

Propagation:

*Type.*—By vegetative cuttings and by division.

*Time to initiate and develop roots.*—About 6 weeks during the spring under outdoor production conditions, average temperature about 15° C.

*Rooting habit.*—Numerous and fine.

Plant description:

*Crop time.*—From cuttings, about 6 months are required to produce fully-grown flowering plants in ground beds.

*Form.*—Upright, narrow inverted triangle, perennial herb.

*Branching habit.*—Basally branching, low to moderate.

*Plant height.*—About 80 to 100 cm.

*Area of spread.*—About 50 cm.

*Vigor.*—Moderate to vigorous.

*Stem.*—Internode length: About 3 to 8 cm. Texture: Slightly pubescent, pubescence more sparse towards apex. Color: 137C.

*Foliage description.*—Arrangement: Single; rosette at base and alternate along flower stems. Quantity per flower stem: Typically about 10. Length: About 7 to 10 cm. Width: About 11 to 15 cm. Aspect: Mostly horizontal. Shape: Palmate. Apex: Acute. Base: Hastate. Margin: Incised, laciniate. Texture: Smooth; sparsely pubescent at veins. Color: Young and mature foliage, upper surface: 137A to 137B. Young and mature foliage, lower surface: 138B to 138C. Venation, upper surface: 137A to 137B. Venation, lower surface: 137B to 138B. Petiole: Length: Basal rosette leaves, about 25 to 35 cm; flower stem leaves, about 5 to 20 cm. Diameter: Basal rosette leaves, about 5 to 4 mm; flower stem leaves, about 2 to 3 mm. Color: 137A to 137B.

Flower description:

*Flower type and habit.*—Single flowers arranged in a raceme; zygomorphic. Self-cleaning.

*Natural flowering season.*—Continuously flowering typically during August through September in the Northern Hemisphere.

*Flower longevity.*—Flowers last about 10 days on the plant or as a cut flower.

*Quantity.*—Freely flowering with about 30 to 35 flowers and flower buds per raceme.

*Fragrance.*—Very faint, typical of species.

*Flower buds* (*about one day before opening*).—Length, excluding spur: About 1.2 to 1.5 cm. Spur length: About 2 to 2.3 cm. Diameter: About 1 cm. Shape: Orbicular to obovate. Rate of opening: About 2 to 4 weeks from visible bud to fully opened flower. Color: Dark blue, 94A to 95B.

*Flower size.*—Diameter: About 3.5 mm. Depth (excluding spur): About 1.5 cm. Spur length: About 2.5 to 3 cm.

*Petals.*—Quantity: Two central petals, opposite with yellow hairs, and three to five other smaller petals. Shape: Two central petals, orbicular to flabellate; other three to five petals, spatulate. Margin: Entire. Length: Two central petals, about 10 mm; other three to five petals, 9 to 12 mm. Width: Two central petals, about 6 to 7 mm; other three to five petals, about 1 cm. Texture: Two central petals, pubescent; other three to five petals, smooth. Color: Two central petals, blue (104B to 105C) with yellow hairs (9A); other three to five petals, creamy white, 155C.

*Sepals.*—Quantity: Five; upper sepal spurred. Shape: Elliptic to obovate. Apex: Obtuse to rounded. Margin: Entire. Length: About 1.8 to 2 cm. Width: About 1.3 to 1.6 cm. Texture: Dull; smooth; somewhat rugose. Color: When opening and fully opened, upper surface: 104B to 105C, changing to 96A to 96B with subsequent development. When opening and fully opened, lower surface: 96B/98B.

*Bracts.*—Quantity: Two. Shape: Linear; apex, acute; margin, entire. Length: About 5 mm. Diameter: About 3 mm. Texture: Smooth; sparsely pubescent. Color: 93A.

*Pedicels.*—Length: About 1 to 2.5 cm. Angle: About 35° to stem. Strength: Moderate to strong. Color: Green, 137A, to dark blue, 103A.

*Reproductive organs.*—Stamens: Stamen number: Numerous, more than 30. Anther attachment: Basifixed. Anther shape: Oblong. Anther size: About 1.5 mm. Anther color: Very close to 103A. Pollen amount: Sparse. Pollen color: Grayish white. Pistils: Pistil number: About three. Pistil length: About 2 to 3 mm. Stigma shape: Club-shaped. Stigma color: Creamy white. Style length: About 2 to 3 mm. Style color: Creamy white. Ovary color: Close to 103A.

*Seed.*—Length: About 2 mm. Diameter: About 2 mm. Color: Dark brown to almost black, close to 202A.

Disease resistance: Under commercial conditions, plants of the new Delphinium have exhibited some resistance to diseases common to Delphinium.

It is claimed:

1. A new and distinct cultivar of Delphinium plant named 'West End Blue', as illustrated and described.

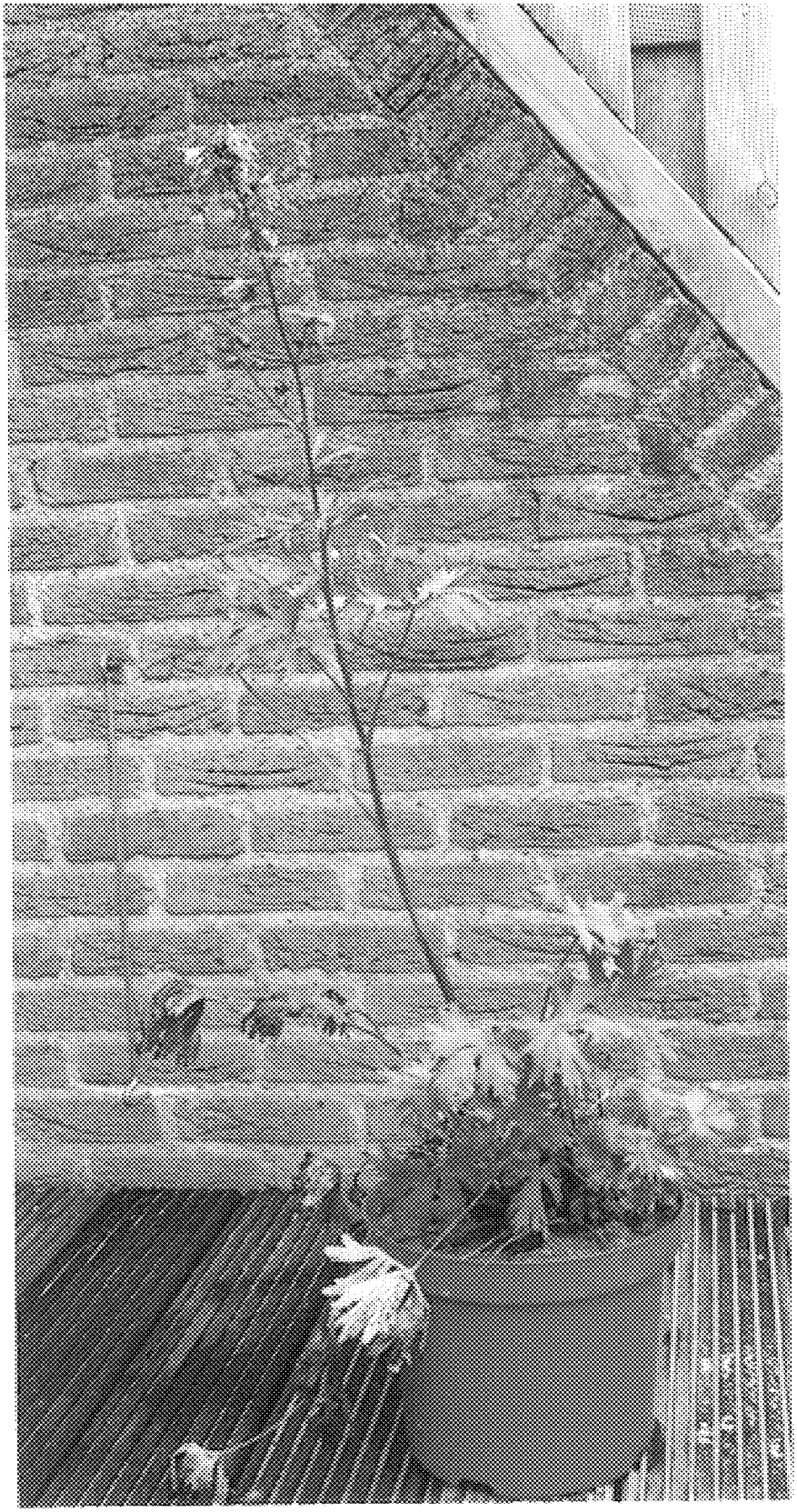

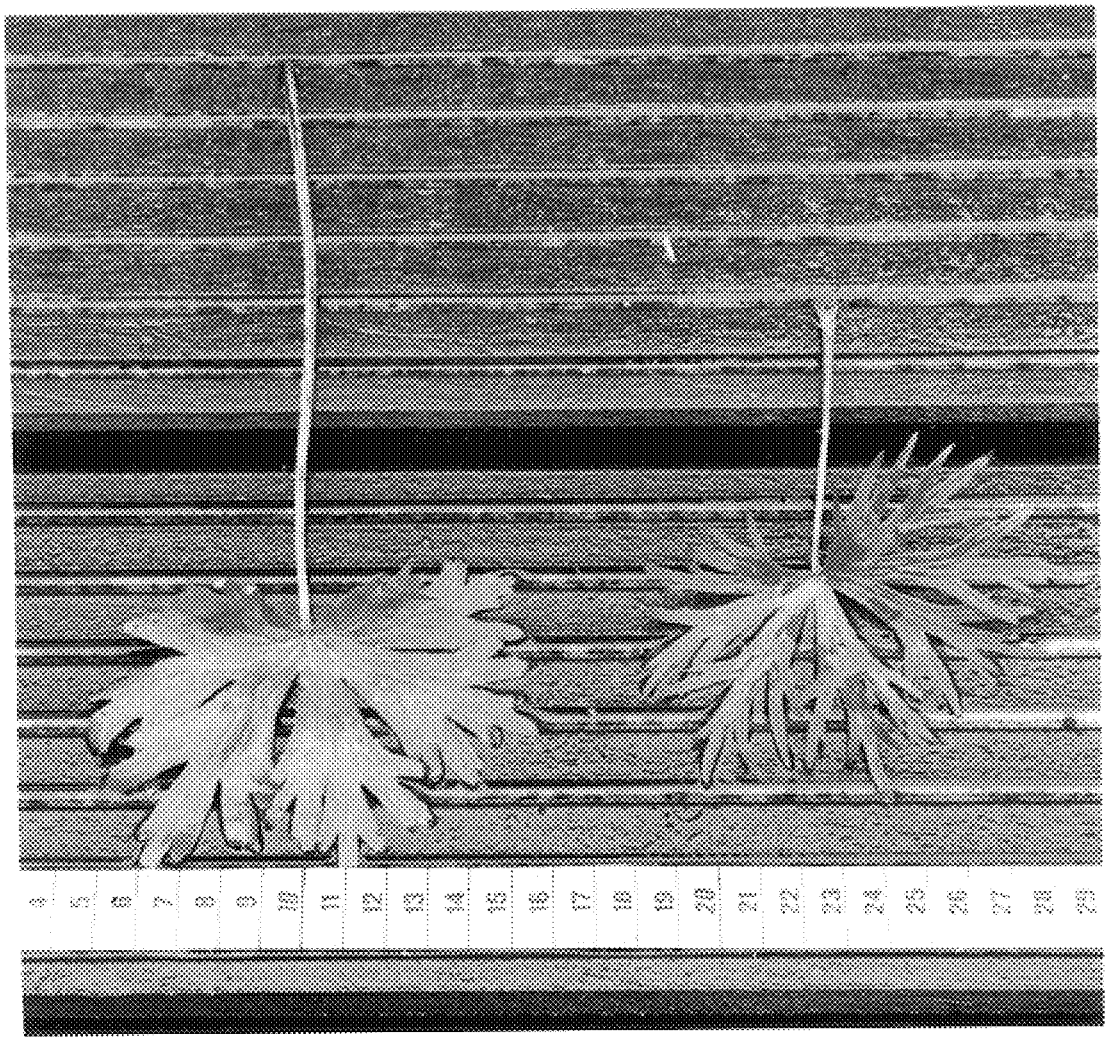

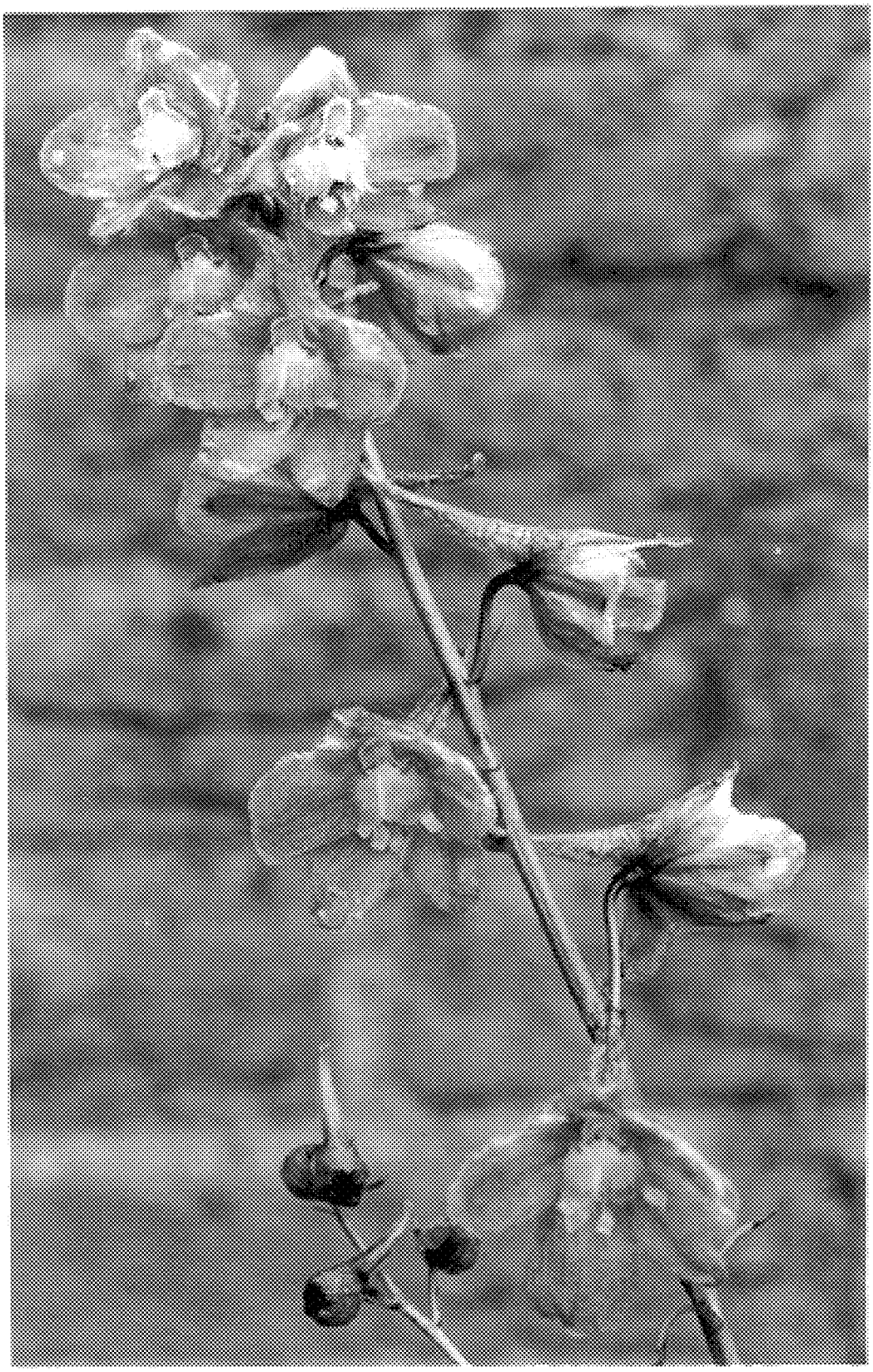

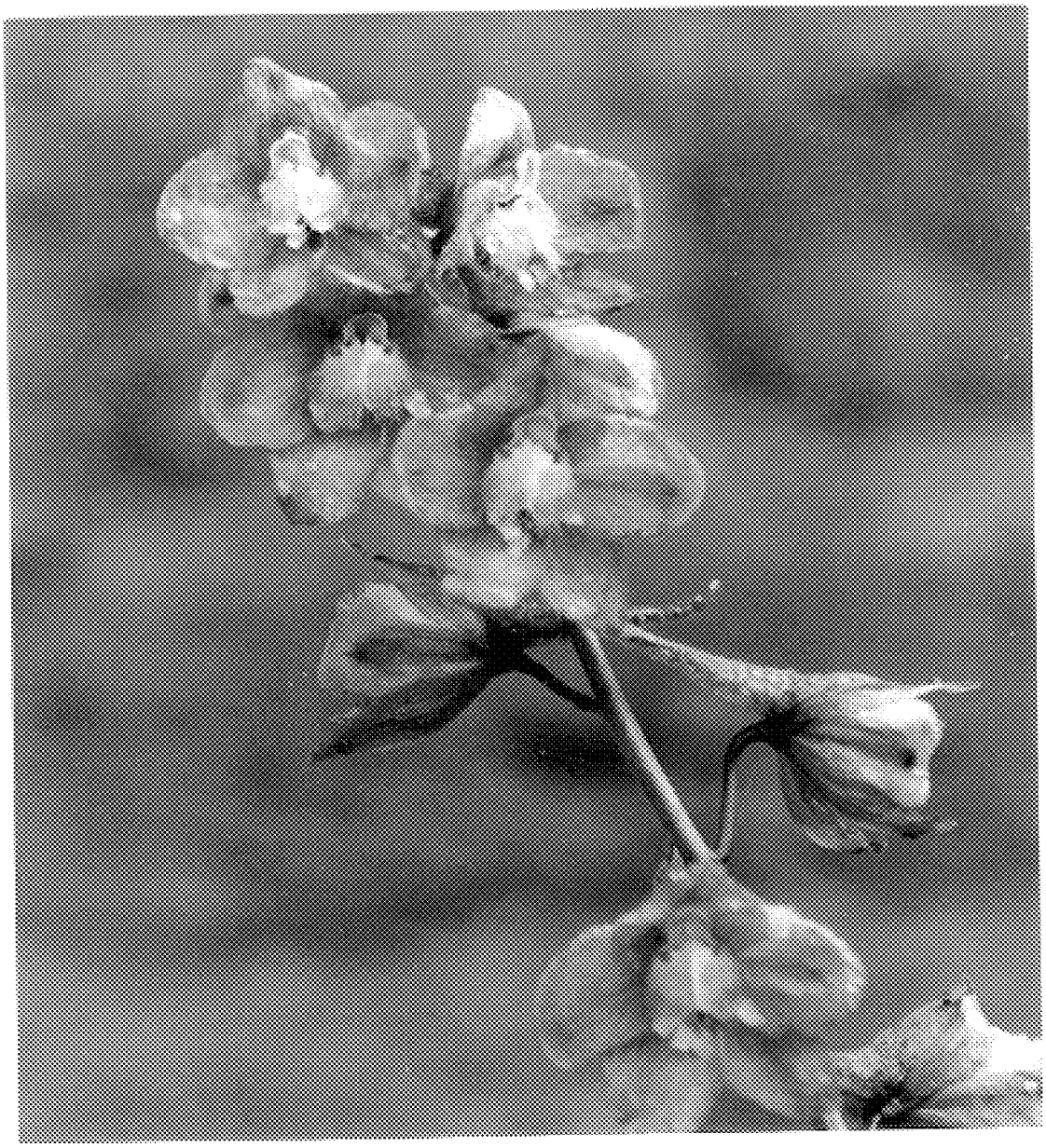

* * * * *